United States Patent [19]

Williams

[11] 4,184,064
[45] Jan. 15, 1980

[54] WATER HEATING MEANS

[75] Inventor: David E. Williams, Hemet, Calif.

[73] Assignee: Amark Industries, Inc., Scanacinty, Calif.

[21] Appl. No.: 855,406

[22] Filed: Nov. 28, 1977

[51] Int. Cl.² ............................................. F24H 1/16
[52] U.S. Cl. ..................................... 219/303; 433/27; 219/307; 219/328; 433/32
[58] Field of Search .................... 32/22, DIG. 3, 28; 219/296, 299, 300, 303, 306, 307, 308, 328, 319, 280; 137/341; 128/256, 257

[56] References Cited

U.S. PATENT DOCUMENTS

| 927,755 | 7/1909 | Robinson | 219/301 |
|---|---|---|---|
| 965,333 | 7/1910 | Robinson | 219/303 |
| 1,631,753 | 6/1927 | Midulla | 137/341 |
| 1,759,774 | 5/1930 | Andriulli | 219/306 |
| 1,958,332 | 5/1934 | Carpenter | 32/28 |
| 2,110,339 | 3/1938 | Pieper | 137/341 |
| 2,117,419 | 5/1938 | Hamrick et al. | 219/306 |
| 2,287,974 | 6/1942 | Cohen | 219/300 |
| 2,878,360 | 3/1959 | Tavender et al. | 219/304 |
| 3,346,957 | 10/1967 | Maurer et al. | 32/22 |
| 3,593,649 | 11/1968 | Novi | 219/306 |

FOREIGN PATENT DOCUMENTS 72800  3/1916  Switzerland ............................. 219/307

Primary Examiner—Russell R. Kinsey
Assistant Examiner—John J. Wilson
Attorney, Agent, or Firm—Georges A. Maxwell

[57] ABSTRACT

A water heater including an elongate tubular case, a block and a plug in spaced relationship in the case defining a chamber, an elongate heater tube with a helical portion within the chamber, and defining a central longitudinal opening, means connecting the ends of the tube with water supply and delivery lines, an elongate resistance heater unit extending longitudinally through said tube, an end extending from one end of the tube, a power supply line extending from a power source to the unit and means to control the supply of power from the line to the unit including a temperature sensing device positioned in the opening defined by the coiled tube and operable to stop and start the flow of power to the unit when the temperature of air in said opening is above and below a set temperature.

6 Claims, 9 Drawing Figures

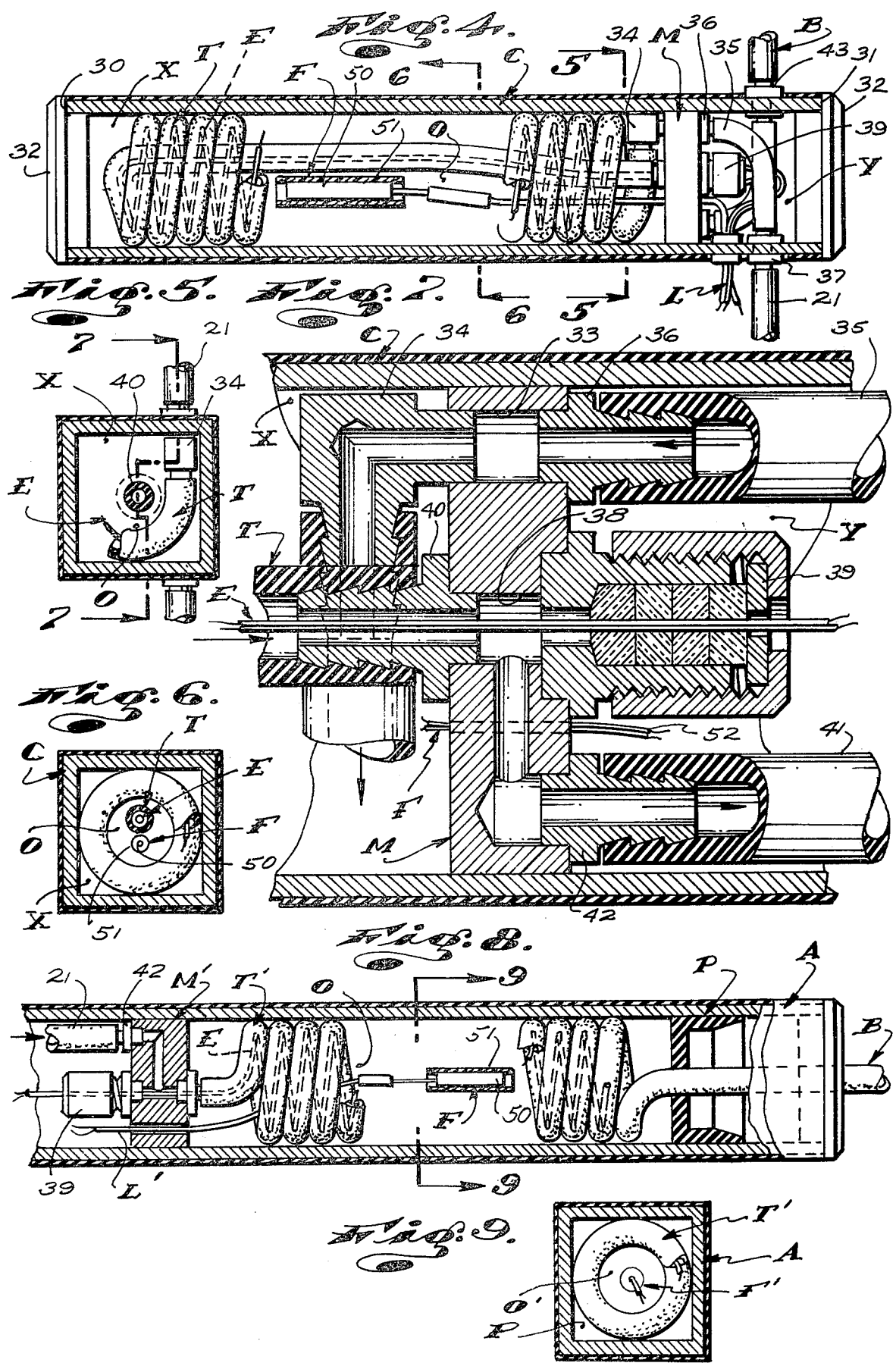

WATER HEATING MEANS

This invention has to do with a water heater and is particularly concerned with an improved water heater for use in combination with a dental irrigating instrument or syringe and with related dental operatory equipment.

In the dental art, manually operable water irrigating instruments or syringes are provided to enable dentists to periodically flush the work site in a patient's mouth with water, to clean the site of grinding and the like.

Dental syringes include manually engageable bodies connected with elongate flexible water supply hoses. The bodies are provided with elongate dispensing nozzles and include manually operable valve means to control the flow of water through and from the nozzles. The water supply hoses commonly extend from the syringes to outlet fittings of water supply means within vertically extending, floor mounted operatory stands or pedestals positioned adjacent chairs or lounge type seats in which patients are seated. The operatory pedestals serve to support instrument carrying trays, lighting means, power driven drills and other dental equipment. The instrument trays are commonly carried by support arms pivotally supported by the pedestals so that the trays can be conveniently moved to and from close and convenient working proximity with the patients seated in the chairs. The trays commonly include hooks or similar fixtures to engage and releasably support the syringes and other equipment, such as drills and the like.

So as to avoid patients experiencing the pain of thermal shock resulting from the directing and application of cold water on highly sensitive areas in their mouths, water supplied to the syringes is commonly heated or tempered to, for example, 100° F.

In the ordinary dental operatory, the hot water supply for the irrigating syringe consists of a hot water supply tank arranged within the pedestal, at or near the base thereof, and connected with the aforementioned water outlet fitting on the pedestal by a hot water delivery pipe. Cold water is delivered into the tank by a cold water supply pipe extending from a remote pressurized water supply, such as a municipal water service system. Water in the supply tank is heated by means of an elongate cartridge type resistance heater which projects freely into the interior of the tank.

While the above noted common type or form of hot water supply for dental syringes has been accepted and is widely used, it is inefficient and often deficient and incapable of supplying water to syringes at a substantially constant or uniform temperature. As a result, it is not infrequent that water which is so cold as to cause pain to patients is delivered by syringes. It has been determined that such variations in water temperature are caused by the dissipation of heat from the pipes and hoses of the irrigating systems into the atmosphere, as they extend from the hot water tanks to the syringes. Adverse fluctuations in temperature are also caused by the mixing and blending of cold water with hot water in the supply tanks, as hot water dispensed therefrom is replaced by cold water. As a result of the mixing together of hot and cold water in the tanks, the temperature of the entire supply of water in the tanks is lowered and that heated water which flows therefrom is at a temperature below the desired operating temperature. Lowering of the temperature of hot water supplies in the above manner, coupled with the normal loss of heat from the system between the hot water tanks and the syringes, results in substantial adverse drops in water temperature at the syringes.

In efforts to overcome the above noted changes in the temperature of water delivered to dental syringes, resulting from the introduction of cold water into the hot water tanks, the water tanks have been made sufficiently large so that the volume of hot water stored therein is sufficiently great so that the normal or anticipated volume of cold water flowing into the tanks is insufficient to cool the hot water excessively. Additionally, the tanks are provided with thick and heavy metal walls to establish heat store means which serve to modulate fluctuations in temperature of the water within the tanks.

The provision of large heavy hot water tanks as noted above requires the use of costly to operate high output resistance heater means and dictates that the tanks be arranged within the normally enlarged base portions of the pedestals or at some location remote from the pedestals and the patients seated in the adjacent chairs. That is, due to the size and weight of the hot water tanks of the character referred to above, it is not practical or feasible to support or mount the tanks on or from the aforementioned instrument trays, in close proximity to the syringes and to the patients.

While excessive fluctuations in the temperature of water in the hot water tanks, resulting from the introduction and mixing of cold water with the hot water therein has been minimized by simply increasing the size of the tanks, fluctuations in the temperature of hot or tempered water at the syringes and from radiation heat loss and the like in the systems between the hot water tanks and the syringes has not been overcome and remains a serious problem.

An object of the present invention is to provide a novel water heater construction for establishing and maintaining a supply of heated water for delivery to a dental syringe wherein volumes of cold water introduced into the heater construction to replace volumes of heated water delivered thereby are not mixed or commingled with the supply of heated water in the construction whereby cooling of heated water in the construction by cold water introduced into said construction does not occur.

Another object of the invention is to provide an improved heater structure which is such that its volumetric capacity or size can be made a small fraction of the volumetric capacity and size of conventional tank type hot water heater having a capability to deliver substantially the same volume of heated water at a uniform elevated temperature.

It is another object of the present invention to provide a water heater structure of a general character referred to wherein the volume of heated water in the construction and volumes of cold water introduced into the construction to be heated, are maintained in an elongate column of limited cross-section which inhibits or prevents mixing or commingling of the volumes of hot and cold water, whereby the temperature of the heated volume of water in and flowing from the downstream end of the column is not altered or cooled by the cold water added to the upstream end of the column.

Yet another object of the present invention is to provide a water heater structure of the character referred to above wherein the elongate column of water is established and maintained by an elongate water heater tube which tube is helically wound to inhibit the establishment of convection currents therein and resulting commingling of hot and cold water and to limit the longitudinal extent of the construction.

Still another object and feature of the invention is to provide a heater construction of the character referred to which includes an elongate electric resistance heating element arranged substantially concentric in and coextensive with the column of water whereby the column of water is heated from within its mass and throughout its longitudinal extent.

It is an object of this invention to provide a construction of the character referred to wherein the helical tube establishing and retaining the column of water is a heat storage means serving to maintain the heated water of the column at a uniform temperature and serving to supplement the function of the heating element and to heat cold water entering the tube to replenish heated water removed from the tube, by stored or residual heat.

It is another object and feature of the present invention to provide a heater structure of the character referred to wherein the adjacent coils of convolutions of the heating tube occur in bearing heat conducting contact with each other whereby stored heat in the tube is conducted directly from one convolution to the next and longitudinally of the coiled structure, from one end to the other whereby the conduction of stored heat longitudinally of the tube for heating cold water entering the tube is materially faster than if different longitudinal portions of the tube were not in heat conducting contact with each other.

It is another object of the present invention to provide a water heater of the general character referred to above wherein the coiled water heater tube is arranged within a closed case or housing whereby the temperature of the atmosphere within the case changes in response to the changes in temperature of the tube within the case and a structure which includes a temperature sensing device within the case responsive to the temperature of the air therein and operable to control the supply of current to the heating element within the tube.

It is an object of this invention to provide a water heater construction of the character referred to wherein the coiled tube and sensing device are arranged within a tubular tray supporting arm of a related dental operatory.

It is an object and feature of the present invention to provide a water heater construction of the character referred to which is small, light and compact and is directly related to and carried by an arm supported operatory instrument tray and is directly connected with the inlet end of the water supply hose for a related dental irrigating instrument or syringe, whereby the heater is in closest practical relationship with the syringe and heat loss, by radiation and the like, between the heater and the syringe is maintained at a minimum.

The foregoing and other objects and features of this invention will be fully understood and will be apparent from the following detailed description of typical preferred forms and applications of the invention throughout which description reference is made to the accompanying drawings in which:

FIG. 4 is a sectional view taken as indicated by line 4—4 on FIG. 2 and rotated 90°;

FIG. 5 is a sectional view taken as indicated by line 5—5 on FIG. 4;

FIG. 6 is a sectional view taken as indicated by line 6—6 on FIG. 4;

FIG. 7 is an enlarged detailed sectional view taken substantially as indicated by line 7—7 on FIG. 5;

FIG. 8 is a sectional view taken as indicated by line 8—8 on FIG. 3; and

FIG. 9 is a sectional view taken as indicated by line 9—9 on FIG. 8.

Figure 1:
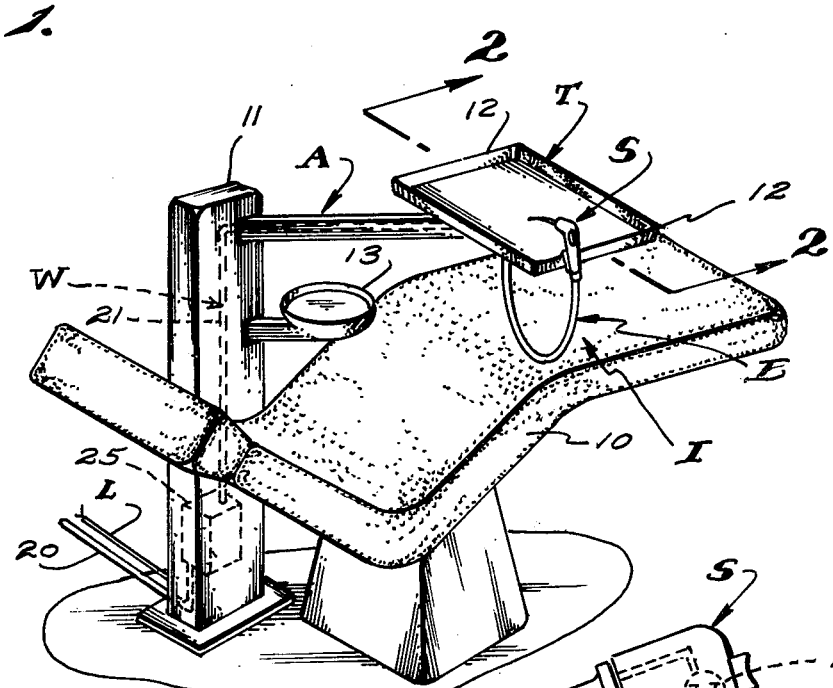
FIG. 1 is a perspective view of a dental operatory apparatus with the present invention related to it.

The water heater structure H provided by the present invention is primarily intended and is particularly suitable for use in the water irrigating means of a dental operatory apparatus such as is shown in FIG. 1 of the drawings.

The apparatus shown in FIG. 1 of the drawings is illustrative of apparatus included in a dental operatory and will hereinafter be referred to as a dental operatory.

The dental operatory includes a floor mounted chair 10 in which a patient to be treated can be seated and a floor mounted pedestal 11 adjacent one side of the chair. The pedestal 11 carries an instrument supporting tray 12, a basin 13 and various other equipment, such as an electrical lamp, drilling equipment and the like (not shown).

The tray T is supported on the outer free end of an elongate horizontal arm A. The inner end of the arm A is pivotally mounted to the pedestal 11 by suitably pivotal mounting means (not shown) whereby the tray can swing horizontally relative to the pedestal and into and out of desired working position, in spaced relationship above and in front of a patient seated in the chair.

The tray 12 is a flat horizontal rectangular or other suitably shaped supporting structure on which various hand tools, cotton swabs, medication and the like can be deposited for ready access and on or from which certain other equipment can be mounted, hooked or otherwise releasably supported.

Included in the equipment related to and supported by the pedestal and tray is an irrigating means I provided to effect flushing or rinsing of the work area in a patient's mouth with water. The irrigating means I includes a manually engageable irrigating instrument or syringe S and an elongate flexible water supply hose B extending between the syringe S and a water supply system W within the pedestal. The syringe S, in accordance with common practice, includes an elongate manually engageable fluid conducting body 15, means coupling the delivery end of the hose B to one end of the body, an elongate water directing nozzle 16 projecting from the other end of the body and a push button operated shut off valve 17 within the body and operable to selectively stop and start the flow of water into, through and from the syringe. In practice, the syring S can be provided with a hangar hook or bracket 18 to facilitate hanging the syringe on the edge of the tray 12 or on some other related supporting structure. Alternatively, the syringe can be releasably engaged in and supported by a suitable hangar, bracket secured to the tray or to some other related supporting structure.

Since the available and serviceable styles and forms of syringes provided by the prior art and since the carrier or releasable support means provided for such syringes, vary widely and since the style or form of syringe and of the support means provided therefor in no way affects the novelty or spirit of the present invention, further detailed description of the syringe and/or the supporting means therefor need not and will not be entered into.

The hose B is a simple, elongate flexible water conducting hose and can be a straight hose structure or a helically wound hose structure such as is shown in the drawings.

The water supply system W, in accordance with common practice, includes a water supply line 20 extending from a pressure water service system (not shown), to the base portion of the pedestal and a delivery line 21 extending vertically in the pedestal from the line 20 to connect with the inlet end of the hose B.

In prior art structures of the general character here concerned with, the water delivery lines terminate at the exterior surface of the pedestal at poins spaced above the base portion thereof and the syringe hoses B are connected therewith by suitable coupling means to extend freely from the pedestals.

In prior structures of the character here concerned with, electric power for various electrically powered means of the operatories is delivered to the pedestals by service lines L extending from a suitable electric power source (not shown) and entering the base portion of the pedestal.

In the prior art structures of the general character here concerned with and as illustrated in the dotted lines in FIG. 1 of the drawings, a tank type water heater 25 is arranged within the lower base portion of the pedestal. The heater 25 is interposed between the lines 20 and 21 and operates to temper or heat the water delivered through the line 21, hose B and the syringe S.

In accordance with the preferred carrying out of the present invention, the tray supporting arm A, the inner end of which is pivotally mounted on the pedestal 11, is tubular and the delivery line 21 of the means W is extended from within the pedestal into and through the arm A to connect with the inlet end of the electric water heater structure H here provided.

The water heater structure H is provided in place of the tank type water heater 25 within the pedestal 11 or the heater 25 remains in and a part of the apparatus to pre-temper the water and supplement the heater structure H.

Figure 2:
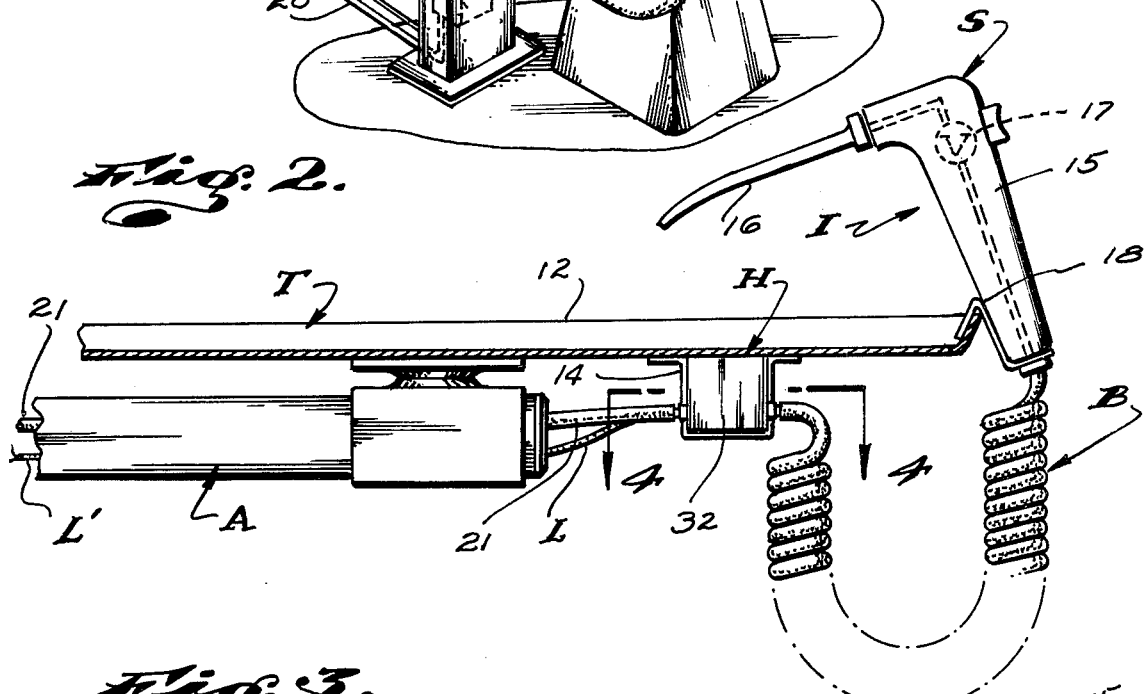
FIG. 2 is a sectional view taken substantially as indicated by line 2—2 on FIG. 1.

In one preferred carrying out of the present invention and as shown in FIGS. 2 and 4 through 7 of the drawings, the heater H is a separate unitized structure located at the exterior of the arm, adjacent to or in close proximity to the tray 12 and to the other free end of the arm. The heater H can be suitably secured to and carried by the arm or can, as shown in FIG. 2 of the drawings, be secured to and/or mounted on the bottom or lower surface of the tray as by means of a suitable mounting bracket 14.

Figure 3:
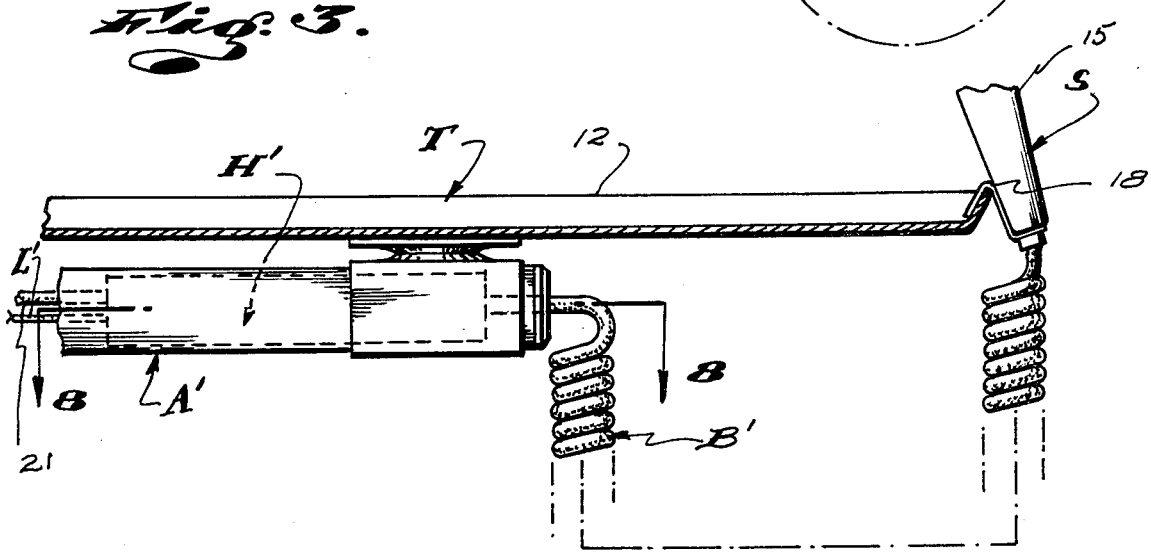
FIG. 3 is a view similar to FIG. 2 showing another embodiment of the invention.

In another form or carrying out of our invention and as illustrated in FIGS. 3, 8 and 9 of the drawings, the heater structure H' is within and is incorporated with the arm A.

The heater structure H shown in FIGS. 2 and 3 through 7 of the drawings is an elongate unit including an elongate tubular body or case C with inner and outer ends 30 and 31. The case C can be established of extruded aluminum tube stock, plastic or any other suitable material. While the case can be of any desired cross-section, it is preferably square in cross-section, as shown in the drawings.

The front and rear ends of the case are closed and sealed by caps or plug-like closures 32. In practice, the closures are preferably molded plastic plugs.

The heater H next includes a manifold block M. The block M is of limited longitudinal extent and corresponds in cross-sectional configuration with the interior cross-section of the case C. The block M is preferably frictionally slidably engaged in the case in spaced relationship between the ends thereof and cooperates therewith and with the plugs 32 to define an inner heating chamber X and an outer chamber Y at what will hereinafter be referred to as the inner and outer ends of the case. The chamber X is of substantial longitudinal extent as compared with the chamber Y.

The heater H next includes an elongate helical water conducting heater duct or tube T arranged in the chamber Y to extend longitudinally thereof and an elongate resistance heater element E arranged in and extending longitudinally through the tube T.

The manifold block M has an axially extending inlet fluid passage 33, the outer end of which is connected with the inlet end of the tube T by means of a fluid coupling 34.

The outer end of the inlet passage 33 is connected with an inlet tube 35 by means of a fluid coupling 36. The tube 35 extends through the chamber Y and connects with the inner end of a fluid conducting water inlet through fitting 37 in one side of the case C.

The outer end of the fitting 37 connects with the outlet end of the delivery line 21 of the water supply means W.

The manifold block next includes an axially inwardly and axially outwardly opening outlet passage 38 and an electric wire packing gland 39.

The passage 38 has an inner end portion substantially concentric with the coiled tube T in the chamber X, an outer end portion laterally offset from said inner end portion and a laterally extending intermediate portion between and connecting the noted inner and outer end portions.

The inner end portion of the passage 38 is connected with the outlet end of the tube T by a fluid coupling 40. The outer end portion of the passage 38 is connected with an outlet tube 41 by means of a fluid coupling 42. The tube 41 extends through the chamber Y and connects with the inner end of a fluid conducting outlet through fitting 43 in a side of the case remote from the fitting 37. The outer end of the fitting 42 connects with the inlet end of the hose B which extends to and carries the noted syringe S.

The packing gland 39 is mounted in the recess entering the outer end of the block M concentric and communicating with the inner end portion of the passage 38 and operates to accommodate and establish a fluid type seal with and about an outer end portion of the resistance heater element E which is arranged in and extends through the passage 38 and the gland, as it extends outwardly from the outlet end of the tube T.

The gland 39 can vary widely in construction and is shown as a conventional screw actuated type of gland structure. It will be apparent that other dissimilar though suitable sealing means, such as potting compound, can replace the packing gland without departing from the spirit of this invention.

The resistance heater element E comprises an elongate doubled length of high resistance wire having free outer end portions and a recurvant inner end. The element enters the outlet end of the duct or tube T, extends longitudinally therethrough to the inlet end portion thereof and thence back to and from the outlet end of the tube, substantially as shown in the drawings.

The outer end portions of the heating element E are provided with low resistance portions which extend through the gland 39 and into the chamber Y where they are connected with or integrally join a power supply line L' for the heater. The low resistance end portions remain cool, in operation, to prevent overheating of the gland 39 and the like.

The line L' is an extension of the line L noted above and extends through the pedestals 11 and arm A, parallel with the line 21 of the means W.

The heating element E includes a high temperature resistant water-proof insulating jacket throughout its entire longitudinal extent whereby the element is safely immersed in the water within and conducted through the tube T.

The heating tube T includes a primary helically wound inlet end portion, the outside diameter of which is substantially equal to the inside dimensions of the body, whereby said primary portion is firmly seated or engaged in the interior of the chamber X as it extends longitudinally thereof.

The adjacent convolutions of the primary portion of the tube T are in bearing heat conducting contact with each other, whereby heat is conducted from one convolution to the next, longitudinally of the tube. The tube T next includes an elongate central outlet or secondary portion which extends longitudinally outwardly from the inner end of the primary portion, through a central opening O defined by said primary portion. The outer free ends of the primary and secondary portions of the tube are those ends of the tube which connect with the manifold block as clearly shown in the drawings and described in the foregoing.

The heater H next includes a temperature responsive control means F for the heater element E to control the supply of power to and operation of the element E to maintain the temperature of water in the tube T at a substantially constant predetermined temperature.

The control means F includes a temperature sensing device such as a thermo responsive switch 50 arranged in the central opening O defined by the primary coiled portion of the tube T, substantially intermediate the ends thereof. The device 50 is responsive to the temperature of the air or atmosphere within said opening O. The device 50 is provided with a suitable heat insulating jacket or shield 51 about its exterior to maintain the device out of heat conducting contact with the tube T. If desired, or necessary, a spider-like switch-supporting and tube-engaging support means can be provided to maintain the device 50 clear or out of heat conducting contact with the tube T.

The device or thermo responsive switch 51 is provided with a pair of conductor lines 52 which extend longitudinally outward in the opening O through a suitable passage provided in the block M and into the chamber Y. The free ends of the lines 52 in the chamber Y are suitably connected in or with the power circuit for the element E.

In one preferred carrying out of the invention where the operating temperature for the construction is preset, the device 51 is a simple thermo responsive switch electrically interposed in one leg or side of the power circuit for the element E. In such a case, the free ends of the lines 52 connect with one leg or end of the element E and with one leg or conductor of the power supply line L', within the chamber Y.

In the case where temperature adjustment is desired, the lines 52 extending from the switch 50 can extend to and connect with a suitable control device or unit (not shown) with which the power lines L' is suitably connected. Such a control unit or device might be arranged within the chamber Y or can be arranged at some location outside and remote from the heater structure H.

In practice, the switch or device 50 can be replaced by any one of several different types of temperature sensing devices, such as thermocouples and can be related with various and different control circuits without departing from the spirit of the present invention.

Novelty in the heater structure H resides in the inter-relationship of the coiled portion of the heating tube T within the chamber X, the heating element E within the tube T and the positioning or arranging of the heat sensing device 50 of the means F within the passage O defined by the tube T.

Upon considering the above noted combination of parts, it is to be noted that the tube T is established of a heat conductive and heat storing material such as copper or plastic and establishes both a hot water reservoir and a heat store. Further, as a result of the heat conducting bearing contact between adjacent convolutions of the tube and the heat storing and conducting characteristics of said tube, heat in the tube is conducted longitudinally thereof at a rate which is materially greater than the rate heat can be conducted longitudinally of a straight tube of like material and of like length.

The electric heating element E extending longitudinally through the tube T heats water in the tube. The heat in the water is conducted into and through the walls or heat storing mass of the tube T.

As a result of the foregoing, it will be apparent that water within the tube is substantially uniformly heated from one end of the tube to the other and that the tube is in turn heated by the water, uniformly from one end thereof to the other.

As previously noted, the coiled portion of the tube T defines the central longitudinal opening O through which the straight outlet end portion of the tube T extends and in which the temperature sensing device or thermo responsive switch 50 is arranged. The temperature of the air in the opening O is heated by the surrounding heat storing coiled portion of the tube to essentially the same temperature as the tube and the water within the tube, whereby the straight portion of the tube extending through said opening and the water therein is maintained at the same temperature. The temperature sensing device or switch 50 arranged in the central opening O is responsive to temperature changes of the air within the opening O.

The closed chamber X in which the tube is arranged and which is defined by the case C, the manifold block M and the plug 32 at the inner end of the case excludes the movement of air into and out of the chamber and in the central opening O.

The above relationship of parts creates an atmosphere within the chamber which is isolated from and substantially unaffected by ambient atmosphere.

By virtue of the square cross-section of the case and the round or circular cross-section of the coiled portion of the tube T, each convolution of the tube establishes point contact with each of the four sides or walls of the case. Such limited, point contact affords a negligible amount of heat conduction from the tube into the case.

That heat which is conducted from the tube to the case is sufficient to heat or temper the case to an extent desirable and effective to prevent chilling of the air or atmosphere within the case but is not sufficient to draw excessive heat from the tube and upset the desired substantially stable temperature of the water in the tube and the air within the case.

When water is caused to flow longitudinally through the tube, it flows as a column therein with little or no mixing of water which occurs at stations spaced longitudinally of the tube. When water is caused to flow longitudinally through the tube from its inlet to its outlet end, hot water flows outwardly through and from the outlet end portion of the tube and cold water flows into the other or inlet end of the tube.

As cool water enters the tube, hot water moving longitudinally in advance thereof is not mixed therewith and cooled thereby and the temperature of the tube about the hot water is not altered. Accordingly, the entire supply of hot water stored in the tube would have to be discharged before any noticeable drop in temperature of water flowing from the tube would be encountered.

As cold water enters the inlet end portion of the tube to replenish dispensed hot water, the heat stored in the inlet end portion of the tube is rapidly absorbed by the cold water. This transferred heat from the tube to the water continues progressively longitudinally of the tube as cold water advances therein to the end that by the time the cold water flowing through the tube reaches the outlet end of the tube, its temperature is raised to near the set or desired or operating temperature of the heater.

When only a limited and small volume of cold water enters the inlet end portion of the tube T to replace a corresponding limited and small amount of hot water dispensed from the tube and stored heat is absorbed by the cold water from adjacent portions of the tube, that heat which is drawn from the tube is replenished or replaced by the stored heat downstream in the tube and conducted longitudinally of the tube from one convolution to the next. Such conduction of heat longitudinally of the coiled portion of the tube is rather slow and normally tends to modulate or prevent any sharp or rapid fluctuations in the temperature in the construction.

When the temperature of the tube T or any portion thereof drops and is lowered by incoming cold water, the temperature of the atmosphere or air in the opening O is caused to drop in response thereto. Since air is a relatively poor heat conductor and the volume of air in the opening O is substantial, the change of temperature of the air is slow and is such that it is rather slow to respond to changes in temperature in the tube. Further, as the temperature of the air in the opening O changes, it tends to change as a whole or substantially uniformly from one end of the opening to the other, whereby the temperature of the air is substantially the average or mean temperature of the whole of the heating tube T.

As a result of the above relationship of parts, operation of the control means F is effectively modulated and such that the element E is not energized until a sufficient portion of the tube T is cooled sufficiently to lower the temperature of the whole of the air in the opening O sufficiently to operate the means F and cause energization of the element E. Further, the element E is not de-energized until the mean temperature of the entire tube and the air in the opening O is raised to set temperature.

The above is highly important as it would be detrimental to the satisfactory operation of the heater construction if the control means were to respond and energize the element E upon the introduction of a limited volume of cold water and the rapid cooling of a limited part of the tube. If such premature response was to be encountered, the hot water remaining in the tube would be overheated before the control means could operate to de-energize the element E or the control means would commence to cycle on and off in such a manner as to adversely affect operation of the heater.

The heating element E is a low voltage low output heater element and is such that heating of the water in the tube, heating of the tube, and heating of the air in the opening O takes place at a notably slower rate than cooling of the construction by the introduction of cold water. The rate of heating is such that the air in the opening O is heated at substantially the same rate as is the water and the tube whereby the control means operates to deenergize the element E as soon as the desired set temperature of the entire structure is reached.

In practice, the length and volume of the tube T, the heat store capacity of the tube T, and the output of the heating element E are proportioned and balanced so that the heater structure will effectively keep pace with and deliver properly heated water at the anticipated maximum rate that water is likely to be dispensed from or by a relating dental irrigating means with which the heater is related. It has been determined that when the heater is properly proportioned and balanced and the anticipated maximum rate of water is conducted through it (intermittently and over a protracted period of time), the heating element E remains energized continuously for protracted periods of time and is only de-energized when use of water is terminated or is suspended for a greater than normal period of time.

As a result of such proportioning and balancing of the heater structure, a minimum volume of water need be heated and a minimum amount of electrical energy is required to heat that water. Further, a minimum amount of energy is lost or wasted.

As a result of the compact and lightweight nature of the heater structure H, it is possible, as shown in FIG. 2 of the drawings, to arrange and mount or support the heater on the instrument tray 12 of a dental operatory and to connect the syringe hose B of the irrigating means I directly with the outlet of the heater. Such an arrangement and relationship of parts not only places the heater close to the syringe S, but makes it possible to employ a hose B which is substantially shorter in length than is required in those cases where such hoses must extend to the pedestals of dental operatories, as is commonly the case.

The close relationship of the heater and the syringe S afforded by the above relationship of parts results in a minimum of heat loss between the heater and the syringe and results in a heater and more convenient to use dental irrigating means.

In the form of heater H' illustrated in FIGS. 3, 8 and 9 of the drawings, the case C' of the heater structure is established by a portion of the tubular tray supporting arm A of the related dental operatory. The tube T' heating element E' and control means F' for the heater H' are substantially the same as like elements and parts of the heater structure H.

In this second form of the invention, the manifold block M' is in the arm or case C' adjacent the inner end of the tube T'. The block M' includes an inlet passage 38' (similar to the outlet passage 38 in the block M' with which the inlet end of the tube T' and the outlet end of the delivery line L', extending longitudinally through the arm A are connected by fittings 42' and 40'. A packing gland 39' (similar to the gland 39 in the first form of the invention) is related to the block M' to accommodate and seal with the element E'.

The outlet end portion of the tube T' rather than being turned to extend through the opening O' established by the tube T' turns and extends longitudinally outward in the case C, and/or arm A and extends through a plug P slidably engaged in the arm or case to position and retain the tube T' in position within the arm or case. The plug P cooperates with the block M' to define the tube accomodating chamber X' of this second form of heater structure.

The plug P can, if desired, be a decorative closure for the outer free end of the arm A, in which case the heater structure is in the terminal end portion of the arm or it can, as shown, be a separate and special plug slidably engaged in the arm, in which case the heater can be located at substantially any location longitudinally of the arm.

In all other major respects and in operation, the heater structure H' is essentially the same as the heater structure H.

With the heater H', the tray supporting arm A of the dental operatory with which the heater is related is utilized as a part or element of the heater whereby a more compact, neater and more attractive operatory is provided.

While the heater structures H and H' here provided are specially designed for use in and are shown and described in combination with particular structure common in most dental operatories, it will be apparent and it is to be understood that the heater structures H and H' are such that they can be advantageously used in any situation where the delivery of heated or tempered water is desired and where, through suitable design, the heater can be made to meet the required operating parameters.

Having described only preferred forms of my invention, I do not wish to be limited to the specific details herein set forth, but wish to reserve to myself any modifications and/or variations that might appear to those skilled in the art and which fall within the scope of the following claims:

Having described my invention, I claim:

1. A water heater including an elongate tubular case, a block engaged within the case and a plug engaged within the case in spaced relationship with the block and cooperating therewith to define an air filled heater chamber, an elongate liquid conducting heater tube established of a material having a high index of heat conductivity and having a helically wound portion substantially coextensive with and arranged within the heater chamber in supported engagement with the case and defining a central longitudinal opening within the chamber, said tube has inlet and outlet ends, connecting means connecting the ends of the tube with water supply and delivery lines, an elongate waterproofed and electrically insulated resistance heater element extending longitudinally through said tube and having an end portion extending from within the tube, a power supply line extending from a power source to said end portion of the heater element and control means to control the supply of power from the power line to the element and including a temperature sensing device positioned in said opening in the chamber and operable to stop and start the flow of power to the element when the temperature of the air within the opening in the chamber drops below and rises above a set temperature, the adjacent convolutions of the helically wound portion of the tube abut against each other in heat conducting bearing engagement with each other.

2. The heater set forth in claim 1 wherein said case is defined by a portion of an elongate tubular member of a structure with which said heater is related and through which said water supply and delivery lines and said power supply line extend.

3. The heater set forth in claim 1 wherein said case is defined of a portion of an elongate tubular instrument tray supporting arm having one end pivotally mounted on a floor mounted pedestal and its other end pivotally engaging and supporting an instrument tray; said delivery line is an elongate flexible line and extends outward from said other end of said arm and connects with a manually engageable irrigating syringe having a manually operable shut-off valve.

4. The structure set forth in claim 1 wherein said temperature sensing device is arranged and supported in said opening defined by the coiled portion of the tube, out of heat conducting contact with said tube.

5. The structure set forth in claim 1 wherein the tube is round in cross-section; said helically wound portion of the tube is round in cross-section and said case is polygonal in cross-section whereby the tube establishes supporting contact with the case at longitudinally spaced points along sides of the case.

6. The structure set forth in claim 5 wherein the temperature sensing device is a thermostatic switch interposed in the power circuit of the heating element in series relationship.

* * * * *